United States Patent [19]
Daleo et al.

[11] Patent Number: 5,557,561
[45] Date of Patent: Sep. 17, 1996

[54] MULTIPLE SIGNAL, DIGITAL DIFFERENTIAL SIGNAL PROCESSOR AND INTERPOLATOR

[76] Inventors: Stephen L. Daleo, 6204 NW. 50th Ter., Parkville, Mo. 64151; David D. Boone, 1104 NE. Long Ridge, Lee's Summit, Mo. 64064

[21] Appl. No.: 342,882

[22] Filed: Nov. 21, 1994

[51] Int. Cl.[6] .................................................. G06J 1/00
[52] U.S. Cl. .................................. 364/602; 364/607
[58] Field of Search .................................... 364/602, 607, 364/723

[56] References Cited

U.S. PATENT DOCUMENTS

| | | | |
|---|---|---|---|
| 3,825,737 | 7/1974 | Croisier | 364/607 |
| 4,070,709 | 1/1978 | Roberts et al. | 364/602 |
| 4,872,127 | 10/1989 | Nolan | 364/602 |
| 5,124,939 | 6/1992 | Mori et al. | 364/602 |
| 5,140,531 | 8/1992 | Engeler | 364/602 |
| 5,146,834 | 9/1992 | Izumisawa et al. | 364/723 |
| 5,210,707 | 5/1993 | Hamamatsu | 364/602 |
| 5,351,087 | 9/1994 | Christopher et al. | 364/723 |

*Primary Examiner*—Tan V. Mai
*Attorney, Agent, or Firm*—G. Joseph Buck

[57] ABSTRACT

A digital, differential signal processor for measuring, digitizing and storing a plurality of analog electrical potentials and for calculating selected potential differentials for display. Each analog, electrical potential is filtered and amplified in a signal conditioner and then its values at successive instants in time are converted to digital data by an analog to digital converter. The digital data that is output by the converter is stored for later recall. A computer calculates each selected differential potential by calculating the numerical difference between the digital data for the two potentials for which the differential is to be determined. The differential, as a function of time, may be displayed in real time or at a later time based upon the stored data. A multiplexer allows one analog to digital converter to process the signals output from a plurality of signal conditioners. The multiplexer, however, causes the instants in time, for which the digital data represents different potentials, to be offset in time with respect to each other. The invention uses numerical interpolation techniques to compensate for the non-simultaneous instants so as to allow calculation of the differentials as if the instants, at which the two potentials were measured, coincided in time.

7 Claims, 4 Drawing Sheets

MULTIPLE SIGNAL, DIGITAL DIFFERENTIAL SIGNAL PROCESSOR AND INTERPOLATOR

BACKGROUND OF THE INVENTION a. Field of the Invention

This invention pertains generally to devices and methods for obtaining and processing differential electrical signals. More particularly, this invention pertains to devices and methods for obtaining and processing differential electrical signals in medical monitoring and diagnostic systems. However, it should be understood that this invention may be used in a broad range of applications where differential electrical signals are measured and recorded or displayed. Thus, although this invention is described in terms of its use in medical monitoring and diagnostic systems, it should be understood that the scope of this invention extends in general to any system in which differential electrical signals are measured and recorded or displayed.

b. Description of the Prior Art

A common technique used for medical diagnosis is the measurement and display as a function of time of the differences between the electrical potentials (voltages) measured at two or more different points on the human body. The electrocardiograph ("ECG") and the electroencephalogram ("EEG") are well known and widely used examples of this technique.

Many sources of electrical potential contribute to the potential that is measured at one point on the human body. Muscular activity and other organic activity throughout the body contribute to the electrical potential, as well as sources such as electrical power systems and other electrical equipment that are external to the human body. In order to remove or cancel out the effects of external sources and the effects of internal sources that are remote from the area in the body that is being examined, one measures the difference in potential (i.e. the potential differential) between two points on the human body which are located in the area of the body being examined. For instance, in a typical ECG examination, a reference wire is attached to the patient and a series of wires are attached to various places on the patient. Differential voltages which represent the differences in potential between various pairs of the wires connected to the chest are measured and displayed. The voltages (or potentials) are sometimes referred to more generally in this specification and in the claims as signals.

Referring to FIG. 1, in the simplest configuration wires 10 and 11 are connected to two electrical potentials (voltages) for which a differential is to be measured. Wires 10 and 11 are connected to a differential amplifier 12 and the output is then recorded and/or displayed as a function of time. As shown in FIG. 2, in the prior art devices buffer amplifiers 21 and signal conditioners 22 typically are connected between each input wire and the associated differential amplifier 23. The buffers provide high impedance inputs which isolate the potentials at the measurement points on the body or other source from the measuring equipment. The signal conditioners amplify the sensed potentials, limit the bandwidths of the signals that are passed to the differential amplifier and may also provide adjustable or fixed offsets in the voltages that are output to the differential amplifier.

In most modern systems, an analog to digital converter 24 converts the analog signal, that is output from the differential amplifier, into a digital signal for display on, and/or storage in, appropriate digital devices. The analog to digital converter 24 outputs a sequence of digital numbers, each number representing the value of the input voltage at an instant in time and the sequence of numbers representing the values of the input voltage at successive instants in time.

In addition to measuring potentials at the body surface, probes have been developed for insertion into the human heart to measure the electrical potentials as a function of time at different points within the heart. A single probe may contain as many as sixty (60) or more separate wires with each wire connected to a separate electrical contact on the surface of the probe. It is likely that the number of contacts on the surface of such probes will be increased substantially in the near future. By measuring the differences in the electrical potentials (the differential voltages) appearing on the wires, the diagnostician is able to obtain a "map" of the electrical activity of that portion of the heart that is in contact with the surface of the probe.

The prior art equipment for measuring the differential voltages suffers from the limitation that the particular differential voltages, that are to be measured and displayed and/or recorded, must be selected prior to the measurement. A pair of wires corresponding to each selected differential is then connected to a differential amplifier and the test is performed the patient. If, after examining the data, the diagnostician wishes to view the difference in potential between two contacts for which the differential was not previously selected, the diagnostician must then make new connections to the differential amplifiers and repeat the tests on the patient. One could avoid the problem of having to perform the test again by using measurement equipment that included a differential amplifier and an analog to digital converter for each possible combination of contacts, taken two at a time. As should be apparent, however, if the probe contains more than a very few contacts, the number of possible combinations, i.e. the number of differentials to be measured, becomes very large and the cost of the related measuring equipment becomes prohibitive.

SUMMARY OF THE INVENTION

Instead of measuring the potential differentials and converting the analog differentials into a digital format and then storing or displaying these differentials, the present invention instead converts each electrical potential (voltage) with respect to a common reference into a digital signal and then stores the digital data representing each voltage as a function of time. The diagnostician may then select which differentials he or she wishes to observe and have the computer calculate the selected differentials and display the selected differentials in real time. If the diagnostician then decides to observe a different differential, he or she simply selects the new differential and the computer calculates the differential based upon the previously stored data and displays the selected differential as a function of time.

The present invention also includes some "conditioning" of the analog signal prior to its conversion into digital data. The conditioning includes buffering, amplifying, band limiting or "offsetting" of the voltage by a selectable, fixed amount or includes at least one or a combination of more than one of these functions.

The preferred embodiment of the present invention also uses a time-multiplexer to time share one or more analog to digital converters between the outputs from a plurality of signal conditioners. The invention utilizes a computational method for interpolating between the digital representations of the values of a first potential at successive instants in time in order to compensate for the fact that the successive instants in time at which the first potential was measured and converted into digital data may be offset in time from the instants in time when the second potential was measured and converted. The offsets are caused by the time-multiplexing of the outputs of a plurality of signal conditioners into a single analog to digital converter.

BRIEF DESCRIPTION OF THE DRAWINGS

FIG. 6 depicts an equipment configuration for the calculation and display of differentials from stored digital representations of the potentials.

DETAILED DESCRIPTION

Figure 1:
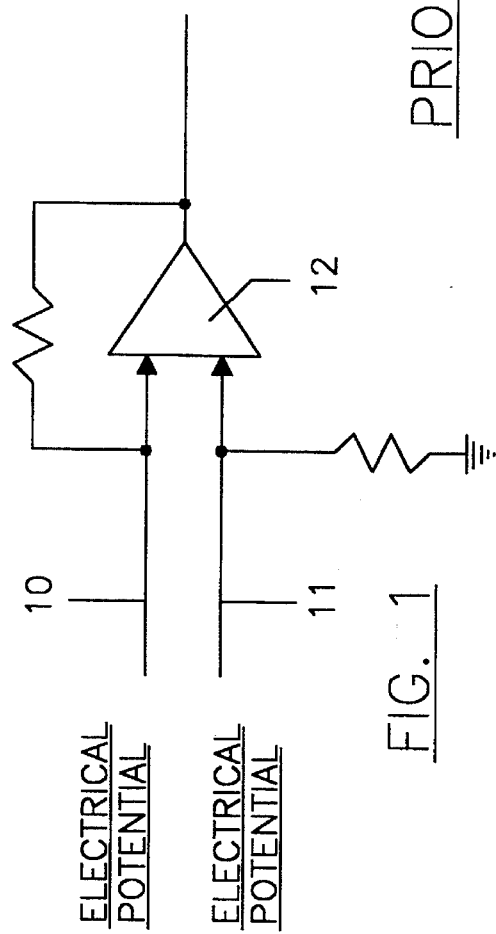
FIG. 1 depicts a prior art device for the analog measurement of a potential differential.
Figure 2:
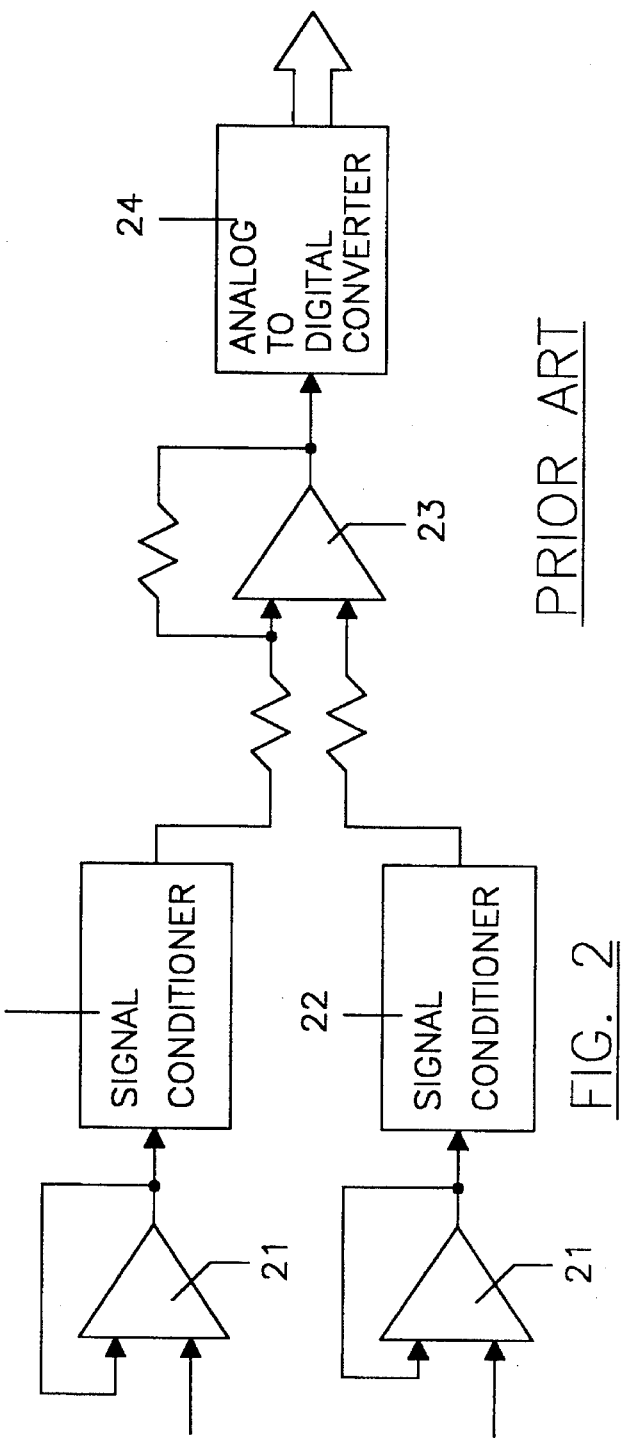
FIG. 2 depicts a prior art device for the measurement of a potential differential and for the conversion of the differential into digital data. The device includes signal conditioners.
Figure 3:
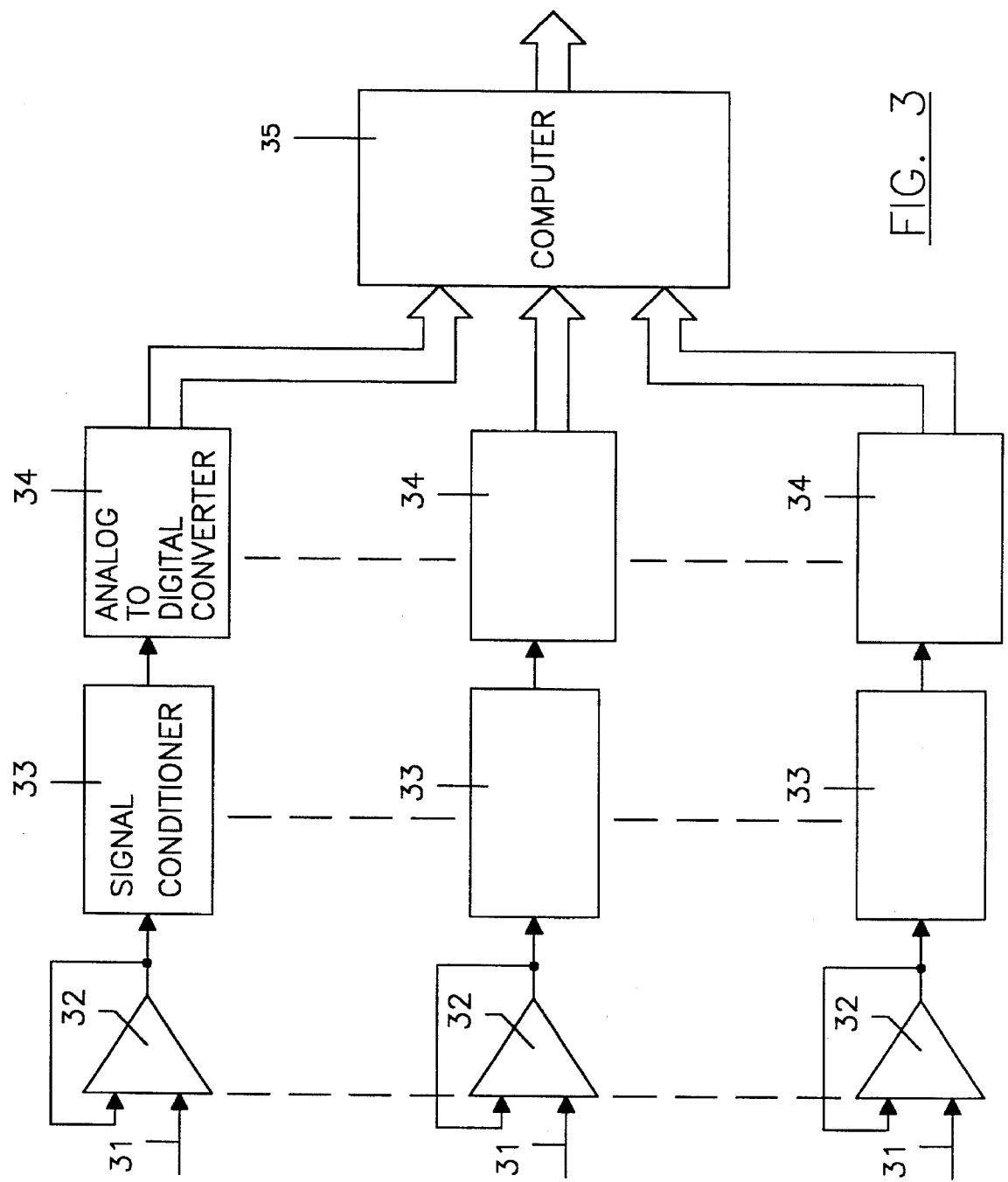
FIG. 3 depicts one embodiment of the invention.

Referring now to FIG. 3, wires 31, which carry the potentials being measured, are input to a plurality of input buffers 32 which are in turn connected to a plurality of signal conditioners 33. In the preferred embodiment depicted in FIG. 3, each buffer 32 amplifies the potential being measured and also provides a high input impedance so as to minimize any "loading" effect of the measuring equipment upon the potentials being measured. Each signal conditioner 33 also includes a low-pass filter which passes the signal of interest while removing higher-frequency noise and other disturbances that are not of interest to the diagnostician. The conditioner also may provide an adjustable, constant (d.c.) offset for the potential that it outputs. As used in the claims, the term analog signal conditioner is intended to mean an element that includes buffering, amplifying, band limiting or offsetting of the voltage by a selectable, fixed amount or that includes at least one or a combination of more than one of these functions. As used in the claims, the term conditioned analog signal is intended to mean a signal that has been buffered, amplified, band limited or offset or that has undergone at least one or a combination of more than one of these processes.

In the embodiment of the invention depicted in FIG. 3, the output from each signal conditioner 33 is input into a separate analog to digital converter 34, which converts converts the analog signal at its input into a sequence of digital numbers. Each number represents the approximate value of the input voltage at an instant in time and the sequence of numbers represents the approximate values of the input voltage at a sequence of instants. The analog to digital converter periodically samples its input voltage and outputs a digital number representing the value of the input voltage at the instant at which the sample is taken.

Computer 35 then receives the digital data from the analog to digital converters 34 and calculates the numerical differences between the sequences of data output from the converters so as to obtain a digital representation, as a function of time, of the difference between the electric potentials that are input to each selected pair of input buffers 32. It should be apparent that by appropriately programming the computer, any combination of differentials may be calculated and output by the computer for storage and/or display.

Figure 4:
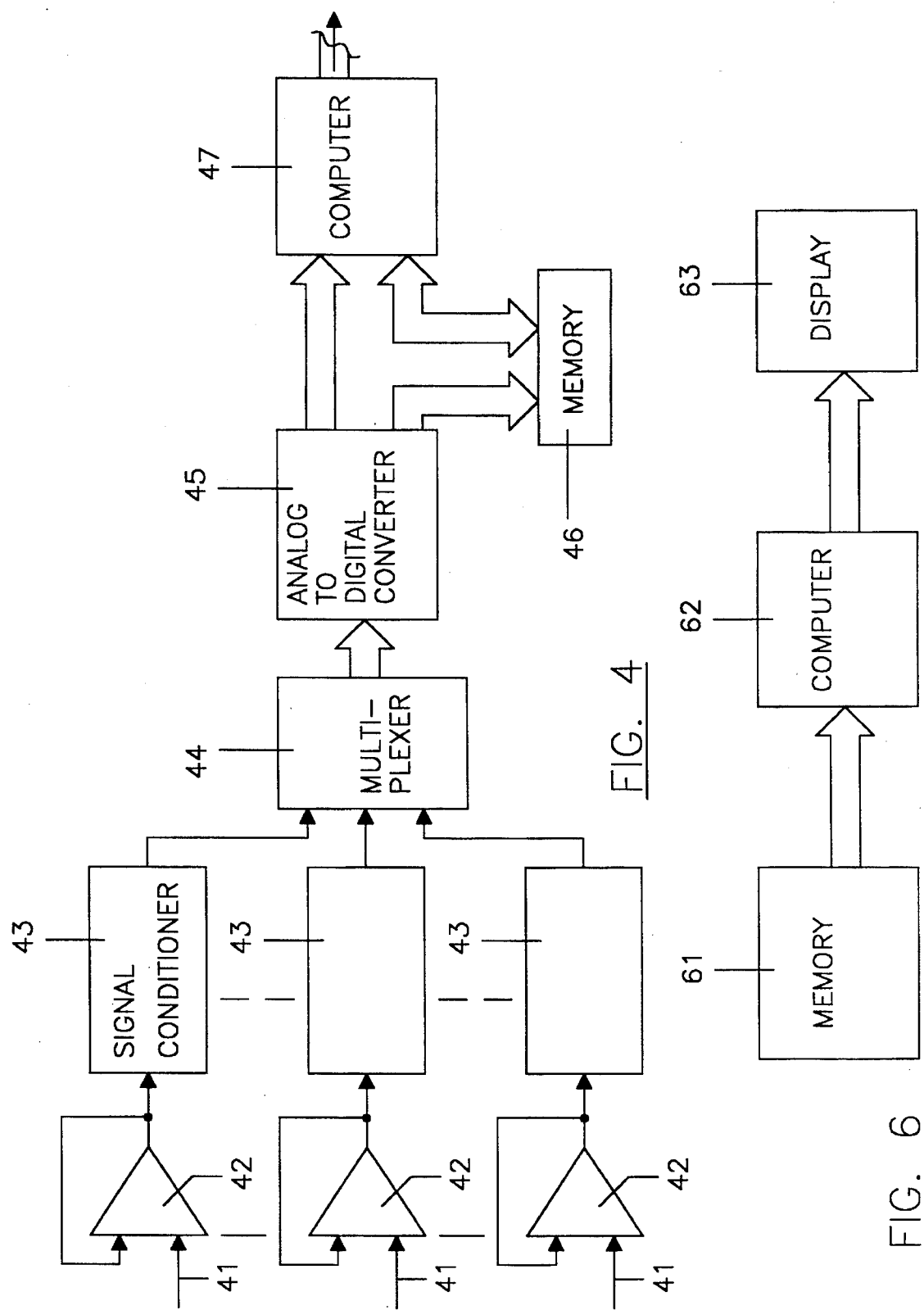
FIG. 4 depicts the preferred embodiment of the invention.

The embodiment of the invention depicted in FIG. 4 differs from that depicted in FIG. 3 in that the outputs from a plurality of signal conditioners 43 are connected to a single multiplexer 44. In FIG. 4. multiplexer 44, in effect, connects its output for a brief period of time to each of its inputs in a rapid time sequence. Multiplexer 44 requires a brief "settling period" or "settling time" for the output to reach the approximate value of the voltage at a particular input following the switch of the connection of its output to a particular input. After the voltage output by multiplexer 44 has "settled", analog to digital converter 45 converts the settled value to a digital number. Thus the settling times of the multiplexer and of the analog to digital converter together determine the time required to obtain a digital representation of the value of the potential at a particular input. Analog to digital converter 45 outputs a sequence of digital numbers which represent the values as a function of time of the voltages input to multiplexer 45, with the numbers for the different input potentials being interlaced in the sequence in accord with the sampling sequence of multiplexer 44.

The sequence of numbers, in digital format, that are output from analog to digital converter 45 are then either stored in memory 46 for later processing by computer 47 or are passed directly to computer 47 for processing, or both. It should be understood that memory 46 could be any type of memory device such, for instance, RAM or a magnetic-disk or memory located within the computer 47 or elsewhere in the system. It also should be understood that the memory 46 may constitute only means for temporarily storing only a sufficient number of values of data to allow interpolation between these values, for example, one or more data registers could, in some instances, provide enough memory for this purpose. Thus although memory 46 is depicted as a separate block, it may, in fact, be an integral part of computer 47. On the other hand, the digital data may be stored for a substantial length of time in temporary or permanent memory before any interpolation or comparisons are performed.

The value of the first input potential as a function of time is represented by a series of numbers, which numbers represent the values of the first potential at a first set of successive instants of time. The value of the second input potential similarly is represented by a second series of numbers which represent the values of the second potential at a second set of successive instants of time. However, due to the sequential manner in which the multiplexer operates, the successive instants in the first set do not coincide in time with the successive instants in the second set, but instead are offset by a small amount in time. As a consequence, if computer 47 is to calculate the differential between the first and second potentials (and if the magnitudes of these potentials are changing significantly between the instants represented by these numbers), then the computer must first, in effect, computationally shift the instants at which the first potential is sampled so that the effective times of these samples will coincide with the instances at which the second potential is sampled. The computer effects this shift in time by interpolating between the numbers that represent successive samples of the first potential so as to obtain digital representations of the first potential at the intermediate instants. Interpolation methods that may be used for this purpose are well known in the art. Erwin Kreyszig, in section 18.4 of Advanced Engineering Mathematics, 3rd Ed., published by Wiley, describes a number of different interpolation methods which may be used for this purpose. It should be understood that the interpolation could be performed on the samples of the first potential or the samples of the second potential, or on both in order to, in effect, obtain values for the first and second potentials for substantially the same instants in time.

The magnitude of the interpolation error, i.e. the difference between the actual magnitude of the signal and the magnitude determined by interpolation, is dependent upon the morphology and frequency content of the input signal and upon the particular algorithm that is used for the interpolation. However, in general, in accord with the Nyquist criteria, the sampling rate should be greater than twice the highest frequency component contained in the input signal. The limit on the highest frequencies may either be inherent in the physical parameters being measured or may be imposed by the low-pass filters in the signal conditioners.

Figure 5:
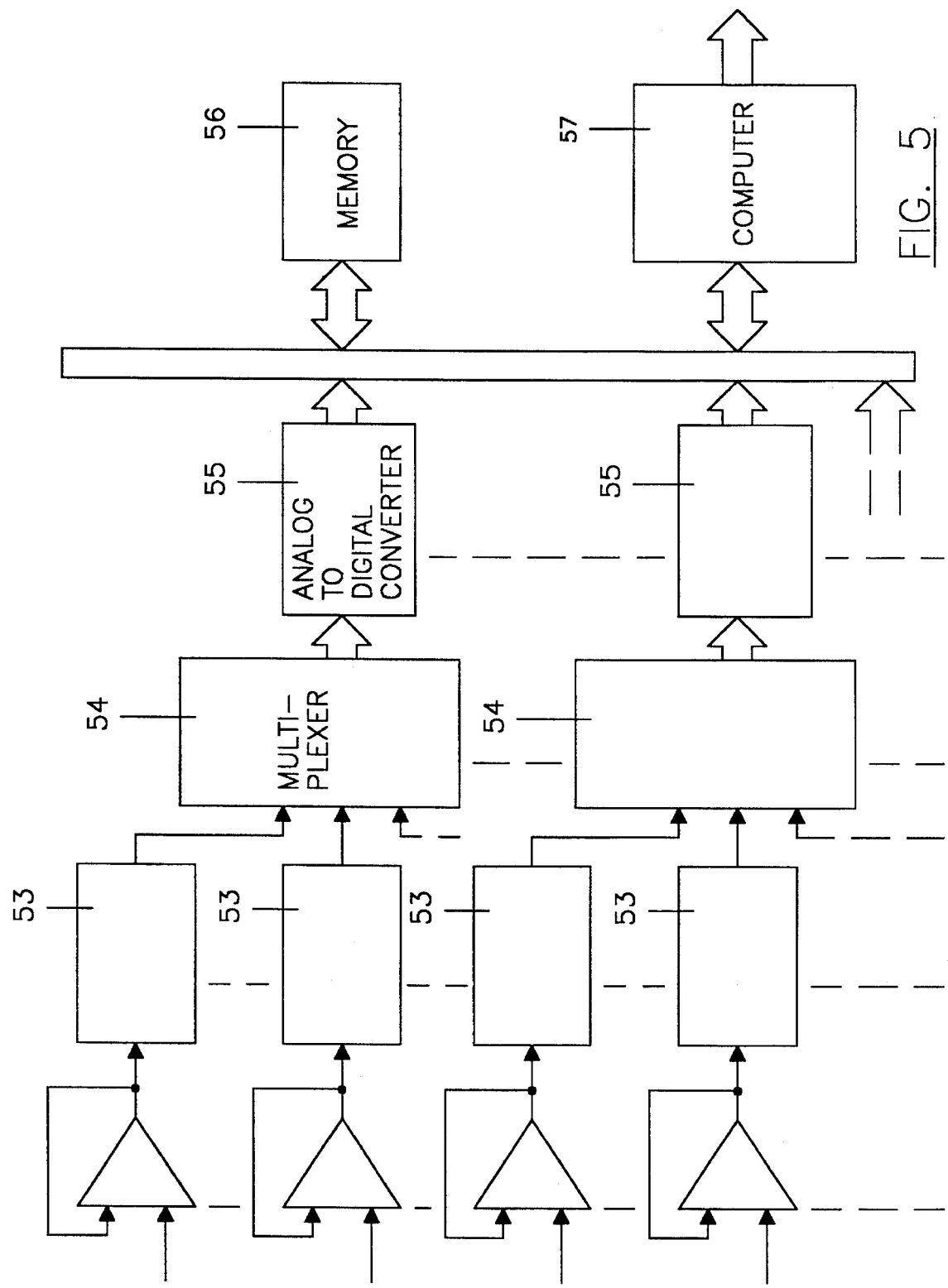
FIG. 5 depicts a generalization of the preferred embodiment.

FIG. 5 depicts a generalization of the preferred embodiment which uses a plurality of multiplexers 57, each of which multiplexers operates to multiplex the outputs from its own group of signal conditioners 53 and to output its multiplexed input into an associated analog to digital converter 55. The sequences of digital numbers output by analog to digital converters 55 are stored in memory 56 and may also be provided directly to computer 57. Computer 57 then calculates the desired differentials for display on appropriate display devices. In those instances where a pair of potentials, for which the differential is to be calculated, were sampled at the same instants in time, computer 57 simply calculates the differential by subtracting data for first potential from the data for the second potential. If the instants in time for the two potentials do not coincide, then computer 57 interpolates the data between successive instants in time so as, in effect, to shift the instants for the first potential to coincide with the instants in time for the second potential as described above with respect to the embodiment depicted in FIG. 4.

FIG. 6 depicts an equipment configuration for display of differentials after the tests have been completed. Computer 62 selects the stored digital data that represents the potentials that comprise the selected differentials, performs any required interpolation and outputs data representing the selected differentials as a function of time to an appropriate display device 63.

Although the invention has been described in terms of its use in medical monitoring and diagnostic equipment, it should be understood that the invention may be used in a wide range of circumstances in which differential potentials are measured and recorded or displayed.

I claim:

1. A device for processing a plurality of analog input signals so as to provide at least one digital differential output signal comprising:

a plurality of analog signal conditioners, each analog signal conditioner having an input and an output and having an analog input signal connected to its input and outputting a conditioned analog signal responsive to the analog input signal, a plurality of analog to digital converters, each converter having an analog input and a digital output, each conditioned analog signal that is output from an analog signal conditioner being input to the input of an analog to digital converter, each analog to digital converter sampling the conditioned analog signal at its input at successive instances in time and outputting digital data representing the values of the samples of the conditioned analog signal at the successive instances in time, a digital computational device, the digital computational device computing for successive instances in time the numerical differences in the digital data representing the values of the samples taken of two of the conditioned analog signals at substantially the same instances of time, and outputting the differences as a digital differential output signal.

2. A device for processing a plurality of analog input signals so as to provide at least one digital differential output signal comprising:

a plurality of analog signal conditioners, each analog signal conditioner having an input and an output and having an analog input signal connected to its input and outputting a conditioned analog signal responsive to the analog input signal connected to its input, a multiplexer having a plurality of inputs and an output, each conditioned analog signal that is output from an analog signal conditioner being input to one of the multiplexer inputs, the multiplexer outputting an analog, time-multiplexed signal responsive to the conditioned analog signals input to its input, an analog to digital converter receiving the output from the multiplexer and sampling at successive instances in time the analog, time-multiplexed signal output from the multiplexer and outputting digital data representing the values of the samples of the conditioned analog signals at the successive instances in time, a digital memory, the digital signal data that is output from the analog to digital converter being stored in the digital memory, a digital interpolator, the digital interpolator, by meant of interpolation between the digital data representing the values of the samples of one of conditioned analog signals, calculating interpolated digital data representing approximate values of the conditioned analog signal for instances in time other than the sampling times, a digital computational device, the digital computational device computing for successive instances in time the numerical differences between the digital data representing the values of the samples taken of one of the conditioned analog signals at successive intervals in time and the interpolated digital data representing approximate values of a second conditioned analog signal at substantially the same successive instances of time and outputting the differences as a digital differential output signal.

3. A device for processing a plurality of analog input signals so as to provide at least one digital differential output signal comprising:

a plurality of analog signal conditioners, each analog signal conditioner having an input and an output and having an analog input signal connected to its input and outputting a conditioned analog signal responsive to the analog input signal connected to its input, a multiplexer having a plurality of inputs and an output, each conditioned analog signal that is output from an analog signal conditioner being input to one of the multiplexer inputs, the multiplexer outputting an analog, time-multiplexed signal responsive to the conditioned analog signals input to its input, an analog to digital converter receiving the output from the multiplexer and sampling at successive instances in time, analog, time-multiplexed signal, output from the multiplexer and outputting digital data representing the values of the samples of the conditioned analog signals at the successive instances in time, a digital memory, the digital signal data that is output from the analog to digital converter being stored in the digital memory, a digital interpolator, the digital interpolator, by means of interpolation between the digital data representing the values of the samples of at least two of the conditioned analog signals, calculating interpolated digital data representing approximate values of at least two of the conditioned analog signals for instances in time other than the sampling times, a digital computational device, the digital computation device computing for successive instances in time the numerical differences between the interpolated digital data representing the values of the samples taken of one of the conditioned analog signals at successive intervals in time and the interpolated digital data representing approximate values of a second conditioned analog signal at substantially the same successive instances of time and outputting the differences as a digital differential output signal.

4. A device for processing first and second analog signals so as to provide a digital output signal approximately representing the numerical difference between values of the first and second analog signals comprising:

a first analog signal conditioner having an input and an output, the first analog signal outputting a first conditioned analog signal from its output responsive to the first analog signal connected to its input, a second analog signal conditioner having an input and an output, the second analog signal outputting a second conditioned analog signal from its output responsive to the second analog signal connected to its input, a first analog to digital converter having an input and an output, the first analog to digital converter sampling the first conditioned analog signal connected to its input at successive instances in time and outputting digital data representing the values of the samples of the first conditioned analog signal, a second analog to digital converter having an input and an output, the second analog to digital converter sampling the second conditioned analog signal connected to its input at successive instances in time and outputting digital data representing the values of the samples of the second conditioned analog signal, a digital computational device, the digital computational device computing for successive instances in time the numerical differences in the digital data output from the first and second analog digital converters and outputting the numerical differences as a digital differential output signal.

5. A device for processing first and second analog signals so as to provide a digital output signal approximately representing the numerical difference between values of the first and second analog signals comprising:

a first analog signal conditioner having an input and an output, the first analog signal outputting a first conditioned analog signal from its output responsive to the first analog signal connected to its input, a second analog signal conditioner having an input and an output, the second analog signal outputting a second conditioned analog signal from its output responsive to the second analog signal connected to its input, a multiplexer having first and second inputs and an output, the multiplexer multiplexing in time the first and second inputs and outputting an analog, time-multiplexed signal responsive to the first conditioned analog signal connected to its first input and to the second conditioned analog signal connected to its second input, an analog to digital converter having an input for receiving the output from the multiplexer, the analog to digital converter sampling at successive instances in time the analog, time-multiplexed signal at its input and outputting digital signal data representing the values of the samples, the successive instances in time for the sampling being coordinated with the multiplexing in time by the multiplexer, a digital memory, the digital signal data that is output from the analog to digital converter being stored in the digital memory, a digital interpolator, the digital interpolator, by means of interpolation between the digital data representing the values of the samples of the first conditioned analog signal, calculating interpolated digital data representing approximate values of the first conditioned analog signal for instances in time approximately coincident with the sampling times for the second conditioned analog signal, a digital computational device, the digital computation device computing and outputting for successive instances in time the numerical differences between the interpolated digital data representing approximate values of the first conditioned analog signal at successive instances in time and the digital data representing values of the second conditioned analog signal at substantially the same successive instances in time.

6. A method for processing a plurality of analog input signals so as to provide at least one digital differential output signal comprising:

conditioning each of the analog input signals so as to provide a plurality of conditioned analog signals, each of which conditioned analog signal is responsive a respective analog input signal, sampling each conditioned analog signal at successive instances in time and converting the samples into digital data representing the values of the samples of the conditioned analog signal at the successive instances in time, computing for successive instances in time the numerical differences in the digital data representing the values of the samples taken of two of the conditioned analog signals at substantially the same instances of time and outputting the differences as a digital differential output signal.

7. A method for processing a plurality of analog input signals so as to provide at least one digital differential output signal comprising:

conditioning each of the analog input signals so as to provide a plurality of conditioned analog signals, each of which conditioned analog signal is responsive to a respective analog input signal, multiplexing the conditioned analog signals and outputting an analog, time-multiplexed signal responsive to the conditioned analog signals, sampling the analog, time-multiplexed signal at successive instances in time and converting the samples into digital data representing the values of the analog, time-multiplexed signal at successive instances of time, interpolating between the digital data representing the values of the samples of at least one of conditioned analog signals to calculate interpolated digital data representing approximate values of the conditioned analog signal for instances in time other than the sampling times, computing for successive instances in time the numerical differences in the digital data representing the values of the samples taken from at least two of the conditioned analog signals at substantially the same instances of time and outputting the differences as a digital differential output signal.

* * * * *